(12) United States Patent
Hoffman

(10) Patent No.: US 6,951,215 B1
(45) Date of Patent: Oct. 4, 2005

(54) DRUG DELIVERY DEVICE FOR ANIMALS

(75) Inventor: Andrew M. Hoffman, Boston, MA (US)

(73) Assignee: Tufts University, Medford, MA (US)

(*) Notice: Subject to any disclaimer, the term of this patent is extended or adjusted under 35 U.S.C. 154(b) by 0 days.

(21) Appl. No.: 09/616,483

(22) Filed: Jul. 14, 2000

(51) Int. Cl.$^7$ .............................................. A61M 11/00
(52) U.S. Cl. ............................ 128/200.22; 128/200.14; 128/200.18; 128/200.23
(58) Field of Search ................... 128/200.14, 200.18, 128/200.22, 200.23, 203.18; 239/338

(56) References Cited

U.S. PATENT DOCUMENTS

| | | | |
|---|---|---|---|
| 2,788,784 A | 4/1957 | Birch et al. ................. | 128/201 |
| 2,829,642 A | 4/1958 | De Melfy ................... | 128/194 |
| 3,812,853 A * | 5/1974 | Crain ....................... | 128/200.17 |
| 3,915,165 A * | 10/1975 | Rambosek et al. ........ | 128/201.11 |
| 4,273,119 A * | 6/1981 | Marchello .................. | 119/832 |
| 4,343,304 A * | 8/1982 | Hickmann .................. | 119/420 |
| 4,470,412 A * | 9/1984 | Nowacki et al. .......... | 128/200.18 |
| 4,546,768 A | 10/1985 | Ferierabend ............... | 128/200.16 |
| 4,577,628 A * | 3/1986 | Hickmann .................. | 128/200.14 |
| 5,012,804 A | 5/1991 | Foley et al. | |
| 5,038,769 A * | 8/1991 | Krauser .................... | 128/203.27 |
| 5,042,467 A * | 8/1991 | Foley ....................... | 128/200.23 |
| 5,062,423 A * | 11/1991 | Matson et al. ............ | 128/200.23 |
| 5,427,089 A | 6/1995 | Kraemer ................... | 128/200.23 |
| 5,485,827 A | 1/1996 | Zapol et al. ............... | 128/200.14 |
| 5,666,948 A | 9/1997 | Matson .................... | 128/200.23 |
| 5,765,548 A * | 6/1998 | Perry ....................... | 128/200.24 |
| 5,855,202 A * | 1/1999 | Andrade .................... | 128/200.14 |
| 5,954,049 A | 9/1999 | Foley et al. .............. | 128/203.29 |
| 5,988,160 A * | 11/1999 | Foley et al. .............. | 128/200.22 |
| 6,026,807 A | 2/2000 | Puderbaugh et al. ..... | 128/200.23 |
| 6,510,818 B2 * | 1/2003 | Barney et al. ............ | 119/831 |

FOREIGN PATENT DOCUMENTS

| | | |
|---|---|---|
| DE | 201 02 803 | 7/2001 |
| EP | 0347779 | 12/1989 |
| EP | 0537991 * | 4/1993 |
| FR | 2481122 | 10/1981 |
| WO | WO 92/10228 * | 6/1992 |
| WO | WO 00/37133 | 6/2000 |
| WO | WO 01/35856 A1 | 5/2001 |

OTHER PUBLICATIONS

Amman et al., Effects of inhaled beclomethasone dipropionate on respiratory function in horses with chronic obstructive pulmonary disease (COPD), Equine Vet J., 1998; 30:(2) 152–157.

Derksen et al., "Use of a hand–held, metered–dose aerosol delivery device to administer pirbuterol acetate to horses with 'heaves'," Equine Vet J., 1996; 28;(4) 306–310.

Hoffman et al., "Management of severe obstructive pulmonary diseaseeith inhaled bronchodilator in a horse," Can Vet J., 1993, 1993;(34):493–495.

Hoffman et al., "Inhaled medications and bronchodilator usage in the horse," Vet Clin of N. Amer.: Equine Prac, 1997; 13:(3) 519–530.

(Continued)

Primary Examiner—Mital Patel
(74) Attorney, Agent, or Firm—Ingrid A. Beattie; Mintz, Levin, Cohn, Ferris, Glovsky and Popeo, P.C.

(57) ABSTRACT

The invention features a drug delivery device which contains a cup-shaped body for enclosing a single external nare of a mammal but does not extend into the nostril of the mammal. The device is used in methods to treat pulmonary diseases. e.g., exercise intolerance, cough, and asthma-like attacks in horses and other animals.

38 Claims, 4 Drawing Sheets

OTHER PUBLICATIONS

Hoffman et al., "Programme of lung function testing horses suspected with small airway disease," Equine Vet Educ., 1999; 11: (6) 322–328.

Rush et al., "Pulmonary function in horses with recurrent airway obstruction after aerosol and parenteral administration of beclomethasone dipropionate and dexamethasone, respectively," Am. J. Vet. Res., 1998; 59:1039–1043.

Rush et al., "Serum corisol concentrations in response to incremental doses of inhaled beclomethase dipropionate," Equine Vet J., 1999; 31: (3) 258–261.

Tesarowski et al., "The rapid and effective administration of a β2–agonist to horses with heaves using compact inhalation device and metered–dose inhalers," Can. Vet. J., 1994; 35:170–173.

* cited by examiner

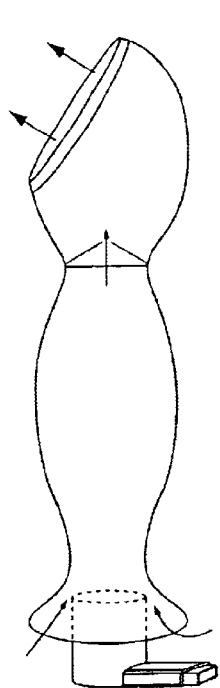
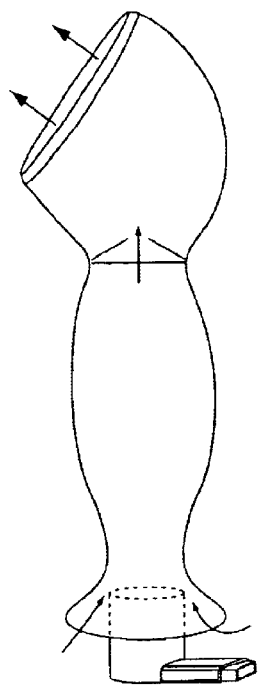
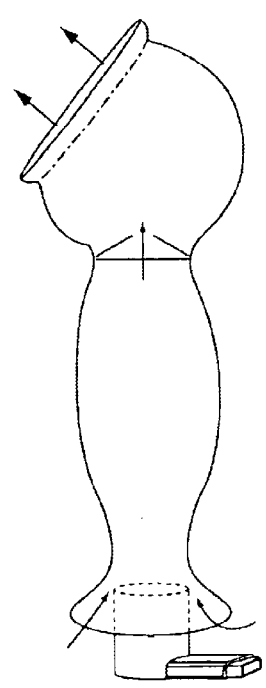
Fig. 3A    Fig. 3B    Fig. 3C
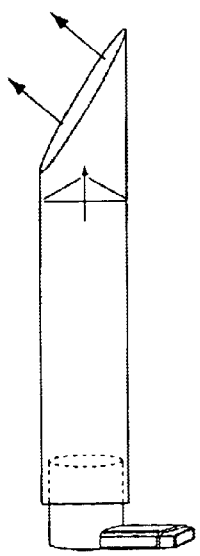
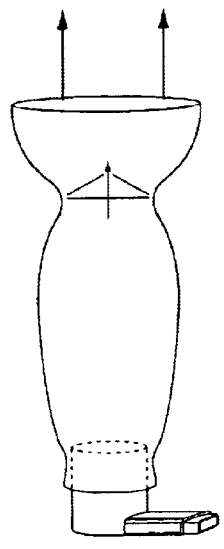
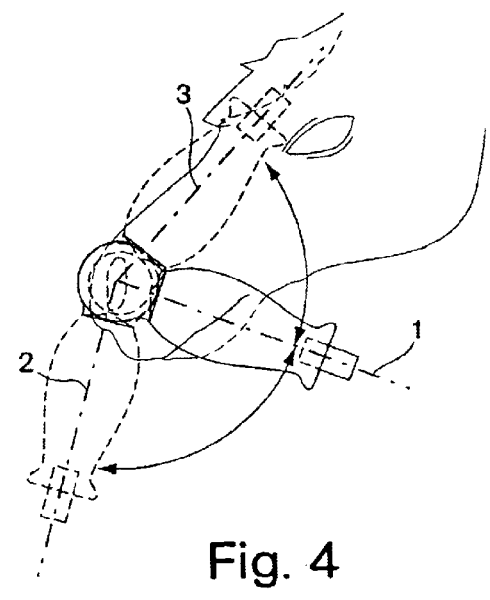
Fig. 3D    Fig. 3E    Fig. 4

DRUG DELIVERY DEVICE FOR ANIMALS

BACKGROUND OF THE INVENTION

Small airway diseases (e.g., small airway inflammatory disease, heaves, and chronic obstructive pulmonary disease) are prevalent causes of exercise intolerance, cough, and asthma-like attacks in horses. These clinical symptoms may be precipitated by progressive allergic reactions to dust found in hay and in the environment, but the cause is not always identified. Traditional management includes minimizing the horse's exposure to dust and conventional hay, bronchodilator treatment for immediate relief, steroid treatment to reduce inflammation and bring about remission, and long-term preventative control with inhaled anti-inflammatory agents.

SUMMARY OF THE INVENTION

The invention features a medical device for administering inhaled drugs. The device is compact, practical, and well-tolerated by animals. Aerosolized therapeutic compositions are delivered to the lung without voluntary cooperation from a horse or other animal to be treated. The drug delivery device contains a cup-shaped body for enclosing a single external nare of a mammal. The device does not extend into the nostril of the mammal. The device does not enclose a second external nare of the animal, thereby allowing the animal to inhale and/or exhale from the nare which is not covered by the device. The device also does not enclose the mouth of the animal and covers only a small portion of the animal's face, thereby improving the animal's tolerance of the device and the methods of therapy utilizing the device. The device, e.g., the opening of the cup-shaped body covers an area from 1–20 square inches, more preferably from 5–10 square inches, and most preferably from 7–9 square inches of the animal's face. For example, a device adapted for use with a horse has an interface or cup-shaped body which covers about 9 square inches of the horse's face. The device is scaled up or down to accommodate the features of the animal with which it is used. For example, the length of the device is in the range of 6–9 inches and the interior volume of the device is approximately 200–500 mililiters.

The device contains a patient-actuated inhalation valve, e.g., a unidirectional valve. The unidirectional valve ensures little or no reverse air flow, a feature that contributes to the efficiency of drug delivery when using the device. Drug proceeds from the drug dispenser, through the device, into a single nostril enclosed by the device, and contacts pulmonary tissue, e.g., small airways, of the animal. The device is suitable to treat vertebrates including humans. Preferably, the device is used to administer medications to mammals with large or widely spaced nares such as horses, cows, sheep, and goats.

Comfort of the animal is enhanced by a flexible interface on the cup-shaped body. The cushioned interface directly contacts the face the animal. The interface or edge of the cup-shaped body is straight, i.e., the plane of the interface is substantially perpendicular to a plane defined by the length of the device Optionally, the cup-shaped body and/or interface which contacts the animal's face is obliquely angled, e.g., the angle of the plane of the interface varies from 1–45 degrees relative to the body of the device. Preferably, the angle is 30–45 degrees relative to the body of the device. The angle is fixed or adjustable.

The device is manufactured with or without a spacer holding chamber. In one embodiment, the device includes a spacer holding chamber which is in communication with the cup-shaped body. The chamber includes a lumen on its distal end for receiving a therapeutic agent. For example, the distal lumen of the chamber is adapted to receive an aerosol container such as a metered-dose inhaler (MDI) cannister. Alternatively, the lumen receives a flow-through drug cannister, e.g., a cannister which contains a therapeutic agent in dry or pressurized form. In another embodiment, the device does not include a drug holding chamber. In the latter embodiment, the cup-shaped body includes a lumen for receiving a drug cannister such as a MDI cannister or a flow-through drug dispenser.

The invention includes methods for preventing or treating a pathological respiratory condition of a mammal using the devices described above. For example, the method is carried out by contacting one nare of the mammal with the device and delivering an effective dose of a therapeutic composition through the device in a single inhaled breath of the mammal. Mammals to be treated include horses, cows, sheep, and goats. The device is scaled up or down in size to accommodate the facial features of larger or smaller animals. The therapeutic composition is administered in the form of a plume of aerosolized particles (e.g., from a pressurized or flow-through container), in the form of a dry powder, or in any other form characterized as having particles of a size suitable for gaining access to small airways of the lung. For example, the particles are not larger than 20 microns in diameter. Preferably, the particles are not larger than 10 microns in size, and more preferably, the particles are 3–5 microns in size. Particles larger than about 20 microns, such as particles generated by a vaporizer and some nebulizers, are not effectively delivered to small airways of the lung. An advantage of the devices of the invention is that the device maintains the small particle size of drugs to be administered (from an MDI cannister or flow-through dry drug container). In contrast, devices which cover the nose and/or mouth of an animal with a mask or rebreathing chamber result in condensation and clumping of particles. The resulting particles are too large to gain access to small airways.

Pathological conditions to be treated or prevented include all types of allergic and nonallergic respiratory reactions including asthma, rhinitis, exercise intolerance, and respiratory inflammation. Small airway diseases (e.g., small airway inflammatory disease, heaves, or recurrent airway obstruction), rhinitis, pharyngitis, bronchospasm, cough, exercise intolerance, pneumonia, pleuropneumonia, chronic bronchitis are treated. Other adverse pulmonary conditions such as those resulting from smoke inhalation or exposure to toxic substances such as organophosphates are also treated using the methods and devices described herein.

One advantage of the invention is that the device does not require insertion in the nose of the animal to be treated. This feature is desirable from the perspective of the animal because nasal insertion is often irritating to the animal's nasal mucosal surface, which area is rich in pain receptors. The design is desirable from the perspective of an owner of the animal or person administering the medication because it avoids the distress of having to place a device in their animal's nose and avoids having to rigorously restrain the animal (a step which may be necessary with a more invasive device, e.g., one which is inserted into an animal's nostril). Thus, animals such as horses are more likely to accept such the noninvasive device described above. Another advantage of the invention is its compactness. The small size of the device allows ease of packing. For example, the device is easily carried on trail rides and in other situations in which storage space is limited.

Yet another advantage is that the device is easily cleaned. Since it is fabricated from a synthetic, nonporous polymeric material and lacks intricate or hard-to-reach parts, rinsing and removal of residual drug, nasal secretions, or other contaminants is simply and quickly accomplished.

Other advantages include the versatility of delivery positions afforded by the angled interface of the device, i.e., a person using the device can choose where they wish to stand while using the device to administer drug. For example, the variety of angles with which the device is manufactured provides the user the opportunity to stand in front of, to the side of, or slightly behind the nares during adminstration of drug. The ability to vary one's position relative to the animal while using the device permits safer handling of the animal to be treated.

The simplicity of the design also allows the device to be made less expensively than other devices, e.g., facemask-type devices, currently in use. Another advantage is that the the holding chamber and low-resistance valve features allow smaller flows (e.g., <1 L/sec) to remove drug particles from the chamber compared to other known devices.

Other features, objects, and advantages of the invention will be apparent from the description and from the claims. Unless defined otherwise, all technical and scientific terms used herein have the same meaning as commonly understood by one of ordinary skill in the art to which this invention belongs. All patents and publications cited in this specification are incorporated by reference.

BRIEF DESCRIPTION OF THE DRAWINGS

FIGS. 3A–E are diagrams showing the flow of aerosol during inspiration. FIGS. 3A–D shown examples of an obliquely angled interface, and FIG. 3E shows a straight interface.

FIG. 4 is a diagram showing angles of interface with a horse's external nares.

FIG. 5B depicts a top view; FIG. 5C depicts a front view; and FIG. 5D depicts a side view.

DETAILED DESCRIPTION OF THE INVENTION

Figure 1:
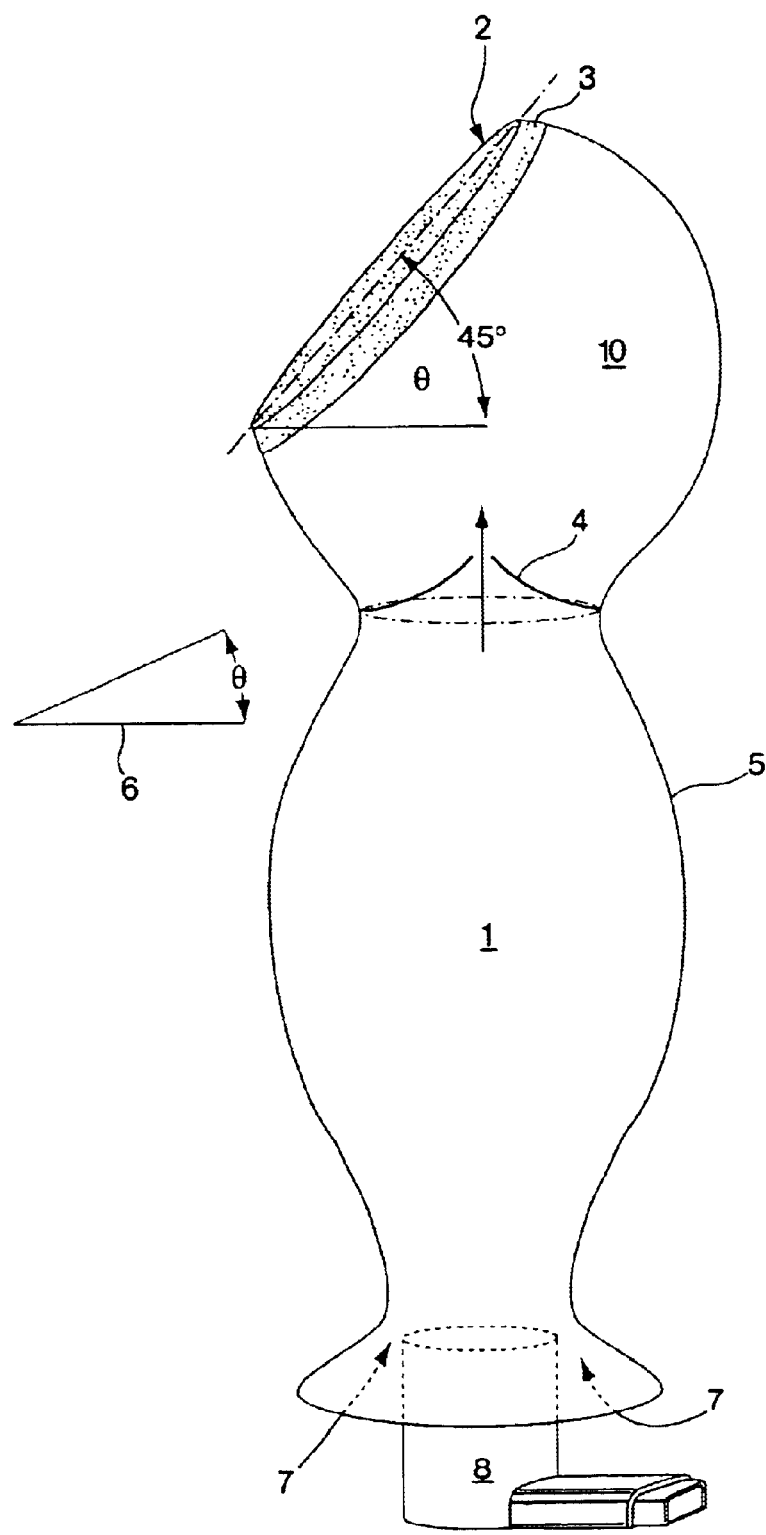
FIG. 1 is a diagram of a drug delivery device with a spacer holding chamber.
Figure 2A:
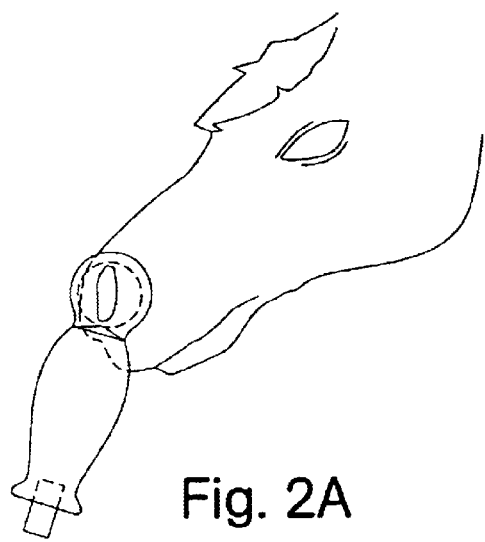
FIGS. 2A–D are diagrams showing a variety of positions in which the delivery device can be used to dispense drug.
Figure 2B:
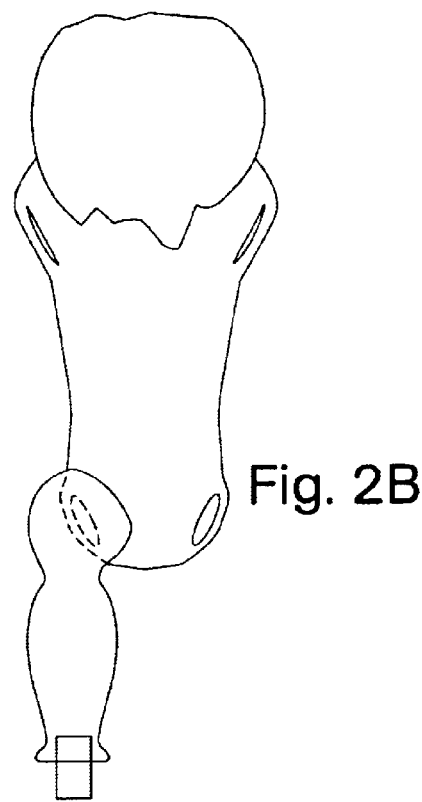
Figure 2C:
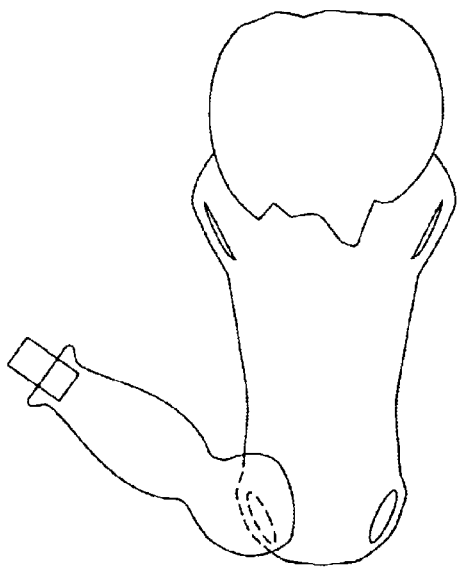
Figure 2D:
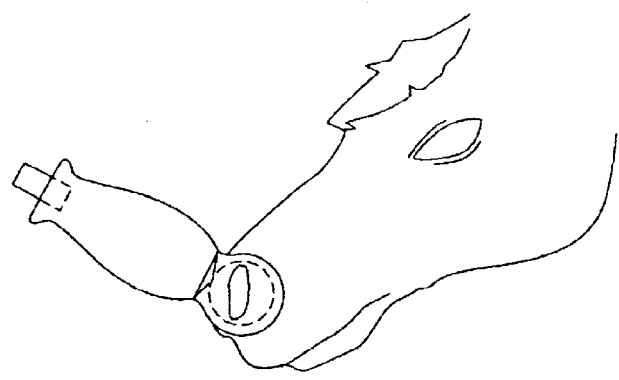
Figure 5A:
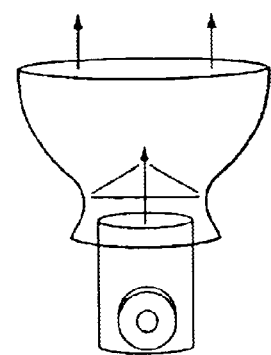
FIGS. 5A–D are diagrams of a drug delivery device without a spacer holding chamber.
Figure 6A:
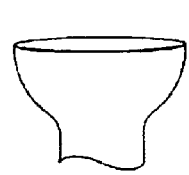
FIGS. 6A–D are diagrams of alternate designs of a drug delivery device with a cup-shaped body but without a spacer holding chamber.
Figure 6B:
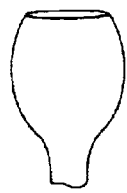
Figure 6C:
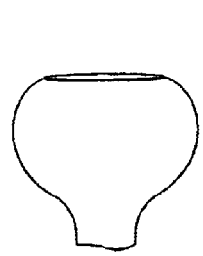
Figure 6D:
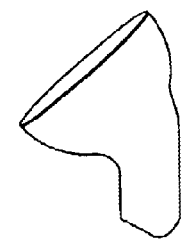

The device described herein is compact and does not require insertion into the nose of an animal. The shell 5 of the device is made from a hard, clear, synthetic material such as plastic. In one example of the device (FIG. 1), the device includes a spacer holding chamber 1. Another example shown in FIG. 6A does not include a spacer holding chamber. In either configuration, the device includes cup-shaped body 10 with a lumen or circular opening 2, which contacts the face of an animal and fits over one of the nares of the animal. A soft interface 3 optionally surrounds the circular opening 2 to cushion the device against the face of the animal to be treated. The soft interface 3 is made from a pliable or flexible material such as foam, rubber or a rubber-like substance. The device contains an inspiratory valve 4 (<0.05 cm $H_2O$/c/sec). The valve is unidirectional, and the unidirectional flow is triggered by inspiration of air by the mammal. Expiratory flow occurs through the other nostril (which nostril is not enclosed by the device) or by removing the device from the face of the animal. The angle 6 between the cup-shaped body and the spacer holding chamber is adjustable and allows a person to stand in various positions for delivering a drug to a mammal. For adjustability of the angle, the junction between the cup-shaped body and the spacer holding chamber is fabricated from a flexible material. A preferred angle 6 is 45 degrees. A lumen 7 located at one end of the spacer holding chamber allows low resistance intakes (<0.05 cm $H_2O$/c/sec) and is adapted to receive a container 8 such as a pMDI or DPI container. The length and width of the device vary depending on the animal to which a drug will be administered. The diameter of the lumen varies to accommodate various containers which are filled with or dispense a therapeutic agent. The device is constructed to dispense a therapeutic dose of drug in a single breath. Table 1 shows examples of per actuation doses of drugs which are delivered by the device.

TABLE 1

| Drug | Per actuation dose |
| --- | --- |
| Albuterol | 90 mcg |
| Ipratropium Br | 10 mcg |
| Fluticasone | 50–220 mcg |
| Bellomethasone | 50–100 mcg |

The cup-shaped body 10 forms contacts the face of the mammal and encloses a single nare. The portion of the cup-shaped body 10 which contacts the face of the animal is optionally angled to allow for a variety of positions during administration of an inhaled drug (FIGS. 2A–D). As shown in FIGS. 3A–E, the flow of an aerosol composition during inspiration by the animal to be treated is from the lumen of the device (which is in communication with the drug container), through a one-way valve, and through the cup-shaped body to a single nare of the patient. A flexible rubber or rubber-like cushion 3 optionally surrounds the portion of the cup-shaped body 10 which contacts the animal provides added comfort for the animal (FIG. 3C). Aerosol flow (as shown by arrows in FIGS. 3A–E) is actuated by inspiration by the animal. Table 2 shows aerosol flow volume using the device with an average adult (500 kg) horse.

| Tidal breathing | Aerosol flow |
| --- | --- |
| Peak Inspiratory Flow (PIF) rate | 2 liters/sec |
| Peak Expiratory Flow (PEF) rate | 2 L/sec |
| Total Volume (TV) | 5–8 L |
| Minute Ventilation (MV) | 100 L/min. |
| Inhalation time (Ti) | 1.5 sec |
| Expiration time (Te) | 2.5 sec |

The cup-shaped body 10 of the device is manufactured in a variety of shaped, e.g., sphere-shaped or cylindrical, and the circular opening 2 may or may not be angled to suit the comfort of the animal or person administering medication (FIGS. 3A–E). For example, FIG. 4 depicts at least 3 angles of interface of the device with a horses's external nare.

Figure 5B:
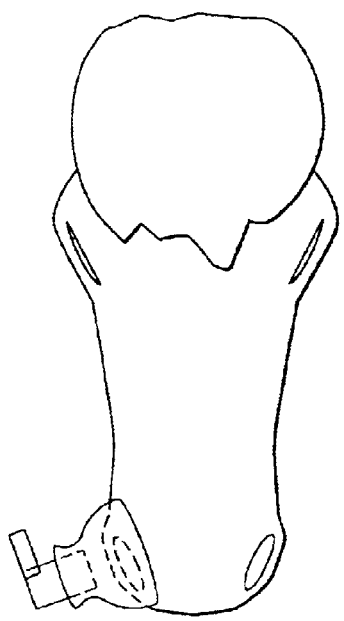
Figure 5C:
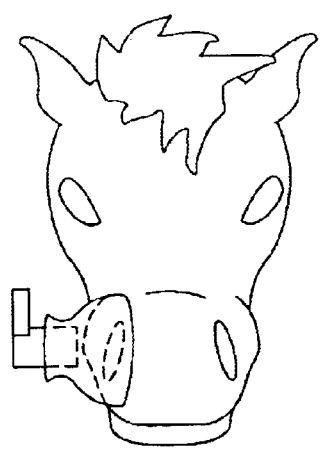
Figure 5D:
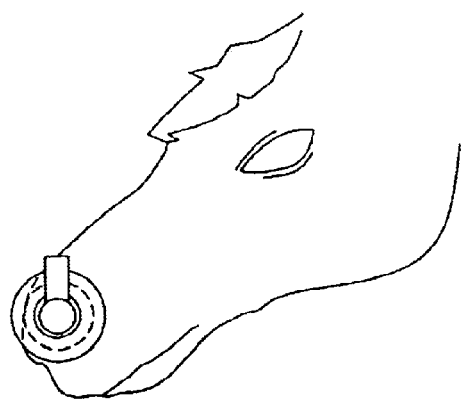

As shown in FIGS. 5A–D and 6A–D, the device need not include a spacer holding chamber. In this example, the medication is dispensed directly into the cup-shaped body 10 from a "flow-through" type drug cannister. Air flows through the drug cannister, through the cup-shaped body, and into the nostril of an animal to be treated (see arrows in FIG. 5A). The end of the device which communicates with the drug cannister optionally contains small holes to allow small amounts of air to pass into the device; alternatively, holes are absent in the end which receives the drug cannister. In the latter example, air flows exclusively through the drug cannister, into the device and into one nostril. A top view of the device deployed to administer drug to one nostril of a horse is shown in FIG. 5D; a front view is shown in FIG. 5C; and a side view is shown in FIG. 5D. The compactness of the device without a spacer holding chamber allows greater portability. As shown in FIGS. 6A–D, the cup-shaped body is manufactured in a variety of shapes and with or without an angled surface by which the device contacts the face of the animal to be treated. The diameter of the interfacing lumen varies with the size of the nares or nostril to be enclosed as well as with the shape of the animal's face. The shape and diameter is altered so as to optimize contact of the device with the animal and to optimize drug delivery.

Delivery of bronchodilator aerosols to horses using an external nasal delivery device indicated that such devices produced beneficial effects comparable to those achieved using a mask device. Mask devices are often not well-tolerated by animals. With a mask-type device, a horse typically alters its breathing to take short breaths. The device described herein does not provoke a change in breathing patterns of the treated animal. The advantages of an external nasal delivery device is small size, versatility of angles of drug delivery, and better tolerance (i.e., less irritation) by the treated animal. Drug delivery by the device of the invention is more efficient than mask-type devices because the flow of drug is directly from the drug container and into the airways of the animal. In constrast, drug administered via a mask-type device must flow around the nostrils to get into the air passage of the nostril, thus reducing the amount of drug effectively administered to the animal. The device described herein does not require an exhalation valve because only one nostril of the animal is covered; the animal exhales with the uncovered nostril or nare.

A one-way valve in the device prevents backflow of medication. The device of the invention is suitable for delivery of aerosols from pressurized cannisters (pMDI). The unidirectional valve of the device permits unidirectional flow of the drug from the chamber, to the device, and finally the respiratory system via the nasal passages, without the need for coordinating the timing of pMDI actuation and inhalation. One advantage of this device is that it offers "virtual breath actuation", is easily cleaned, and only requires that a device is placed on a small portion of the animal's face, i.e., the device covers only one nostril.

Existing drug delivery devices require the user to precisely time drug dispensation with the time of inhalation of the animal to be treated, i.e., the user must deploy a triggering device to actuate drug in synchrony with inhalation. In contrast, the device described herein is breath-actuated, thereby avoiding having to synchronize drug actuation with inhaled breaths. Previously described breath-activated devices are large, expensive, and cumbersome to use. Often such devices cover both nares of a horse (and in some devices, both nares as well as the mouth of a horse), a situation which causes the horse to gasp. Other such devices employ a bag or chamber which covers both nares, a portion of which fits into a horse's mouth like a bit or bridle, and a valve for ejection of exhaled air and/or inhalation of ambient air. Bridle-like devices are typically not well-tolerated by animals such as horses. The device of the invention covers only one nare (not both nares) of the horse and lacks an exhalation valve, thereby improving efficiency of drug delivery and tolerance of the animal to be treated.

Some drug delivery devices require insertion of at least a portion of the device into the nose or nostril of the animal to be treated. In such devices, the drug may be actuated through a bulb and stem, which acts like a holding chamber, and is placed within one nostril, pointing distally. The drug is inhaled with air that flows through the bulb-stem chamber during inhalation. The disadvantage of the such system is the need to place the device in the nose, and the tendency for asynchrony between the actuation of the cannister and the animal's inhalation, resulting in drug wastage.

The device described herein is designed to deliver drug from a pressurized MDI container. Such containers produce small particles, e.g., particles having an average diameter from 1.0 micron to 5.0 microns, whereas vaporizers produce drug particles which are too large to gain access to the lung of the animal to be treated. Some devices also contain a rebreathing chamber and/or an inlet valve for fresh air. Exhalation into the same chamber into which drug is initially delivered causes the drug particles to condense, i.e., become larger, further decreasing the efficiency of drug delivery to the lung and small airways of the animal. Repeated inhalation/exhalation cycles further decrease the efficiency of drug delivery. The device of the invention lacks a rebreathing chamber and delivers small particles of drug in a single effective dose in a single breath inhalation. The device is also suitable for use with dry powders or any other particles that are actuated or nebulized into the holding chamber.

The devices described herein are composed of clear solid plastic or similar material. Preferably, the device is molded from a synthetic nonporous polymeric material ith minimal electrostatic properties, e.g., polyurethane or polyethylene.

EXAMPLE 1

Drug Delivery Device with a Holding Chamber

Device 1 incorporates a holding chamber. The size and features of Device 1 are shown in FIG. 1. The device is applicable to delivery of pMDI aerosols, since these require a spacer chamber for holding the drug in a cloud suspension prior to inhalation. A one-way valve is used to separate the holding chamber from a patient interface, which is angled to allow the user to stand off to the side, yet minimize the angle of delivery and therefore maximize deposition of drug in the respiratory system. Device 1 has small holes on the proximal (PMDI) end, which allow air to flow through the chamber to evacuate the drug into the respiratory system during inhalation. On the distal end, the interface mushrooms to cover the nare on one side (either side) of the horse. The circular opening allows for a number of angles of attachment (FIGS. 2A–E and 3A–E). The interface optionally includes a soft rubber or latex boot for comfort and better conformation to the shape of the patient's face. The inspiratory valve creates very little resistance (<1 cm $H_2O$), to afford maximal opening during inspiration. Expiratory flow is through the opposite nostril, so the inhaler can stay on the face as long as desired without interruption of breathing or drub deliveries. Device 1 is also used for delivery of dry powders or flow-though powders or flow-actuated aerosols of any type.

EXAMPLE 2

Compact Drug Delivery Device without Holding Chamber

Device 2 does not require a holding (i.e., spacer) chamber, and therefore is a collapsed version of Device 1. There is no inhalation valve, since the drug is swept with flow through the drug cannister. The drug cannisters used possesses a flow-through characteristic. The device is also applicable to dry powder or propellant-based flow-through drug cannisters. There is no need for holes in the proximal end to accommodate flow in Device 2, since it is desirable to divert flow through the drug cannister. Device 2 is simply pressed against one of the nares, and with the next inhalation, a dose of the drug exits the cannister, into a short plastic interface space (cup-shaped body), and quickly from there into the horse during inhalation. The process can be repeated on the next inhalation without delay. Exhalation is achieved through the opposite nostril, or by removing the device. Device 2 is even more compact than Device 1, and highly efficient, since it requires only normal breathing and no drug is wasted in a holding chamber. As there is no significant delay in delivery (i.e. the drug is delivered directly from cannister to patient), there is little or not chance of losing drug to evaporation or environmental degradation. The horse can not exhale through the chamber, since there is no flow permitted in this direction.

The devices described here are not limited to the designs in this description, in that there size, angulation of the interface, materials, and dimensions are variable to accommodate the particular features of the patient. For example, the devices are adapted for use in any small or large animal (e.g., a horse), with variation in size and angulation appropriate to species.

Therapeutic Administration

Animals to be treated are suffering from or at risk of developing a pathological respiratory condition. Such conditions or predispositions thereto are diagnosed using methods known in the art. Methods of treatment include administration of aerosolized particles of drug or drug in the form of dry powders, solutions, or aqueous suspensions. Drugs to be administered include anti-inflammatories and bronchodilators such as albuterol (available from Schering Corporation under the PROVENTIL™.

The devices are useful for providing measured amounts of aerosolized therapeutic agents. Drugs are aerosolized using an MDI drug dispenser. Such dispensers deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Alternatively, drugs are dispensed into the device using a flow-through drug cannister. Such dry-powder inhalers are either breath activated or delivered by air or gas pressure such as the dry-powder inhaler described in PCT/US92/05225. Other drug dispensers which are used with the drug delivery device of the invention include a TURBUHALER™ (available from Astra Pharmaceutical Products, Inc.) or a ROTAHALER™ (available from Allen & Hanburys) which may be used to deliver the aerosolized mometasone furoate as a finely milled powder.

Doses of aerosolized or dry drugs and the treatment regimen may vary depending on the age, sex and medical history of the subject being treated, the severity of the specific asthmatic or non-malignant pulmonary disease condition and the tolerance of subject to the treatment regimen as evidenced by local toxicity (e.g., nasal irritation and/or bleeding) and by systemic side-effects. Adjustments in dose and treatment regimens are made according to methods well known the art.

For treatment of diseases of the upper or lower airway passages, the amount of drug administered is a dose that is clinically effective to reduce the symptoms of the disease or condition being treated. For example, a drug is administered in a dose range of about 10 to 5000 micrograms ("mcg")/day, 10 to 4000 mcg/day, 10 to 2000 mcg/day, 25–1000 mcg/day, 25 to 400 mcg/day, 25–200 mcg/day, 25–100 mcg/day or 25–50 mcg/day in single or divided doses. For example, a daily total dose of for a horse is 5 puffs (each breath from the chamber removes one puff). For albuterol, the does is 450 mcg, 200 mcg of drug. Similarly, a total daily dose of Ipratropium Br is 90 mcg; total daily dose Fluticasone is 1.1 mg, 500 mcg; and 200–500 mcg for Bellomethasone. Beclomethasone is administered at a dose of 100 mcg/puff, and salmeterol is adminsitered at a dose of 21 mcg/puff. Clinical effectiveness is assessed by observing a reduction in nasal symptoms (e.g., sneezing, itching, congestion, and discharge). Effectiveness is also determined by decreased effort of breathing, improved arterial blood oxygenation, or improved lung mechanics such as a decrease in pulmonary resistance or maximum change in transpulmonary pressure. These indices are monitored using standard lung function tests.

The foregoing description has been presented only for the purposes of illustration and is not intended to limit the invention to the precise form disclosed, but by the claims appended hereto. Other embodiments are within the following claims.

What is claimed is:

1. A method for preventing or treating a respiratory condition of a mammal, comprising contacting one nare of said mammal with a drug delivery device for a mammal and delivering an effective dose of a therapeutic composition through said device in a single inhaled breath of said mammal, wherein said device comprises a cup-shaped body for enclosing only one external nare, an interfacing lumen the diameter of which does not enclose a second external nare of said mammal, and a unidirectional inhalation valve;

does not extend into the nostril of said mammal; and lacks an exhalation valve.

2. The method of claim 1, wherein said mammal is selected from the group consisting of a horse, a cow, a sheep, and a goat.

3. The method of claim 1, wherein said mammal is a horse.

4. The method of claim 1, wherein said therapeutic composition is administered in the form of a plume of aerosolized particles.

5. The method of claim 4, wherein said particles do not exceed 10 microns in size and wherein said particles are delivered to small airways of the lung.

6. The method of claim 4, wherein said particles are in the size range of 3–5 microns and wherein said particles are delivered to small airways of the lung.

7. The method of claim 1, wherein said therapeutic composition is administered in the form of a dry powder.

8. The method of claim 1, wherein said device does not enclose the mouth of said mammal.

9. The method of claim 1, wherein said device comprises a patient-actuated inhalation valve.

10. The method of claim 1, wherein said cup-shaped body comprises a flexible interface for contacting the face said mammal.

11. The method of claim 10, wherein said interface is angled.

12. The method of claim 10, wherein said interface is straight.

13. The method of claim 1, wherein said device comprises a spacer holding chamber, said chamber being in communication with said cup-shaped body.

14. The method of claim 13, wherein said chamber comprises a lumen for receiving a therapeutic agent.

15. The method of claim 14, wherein said lumen is adapted to receive an aerosol container.

16. The method of claim 14, wherein said lumen is adapted to receive a metered-dose inhaler (MDI) cannister.

17. The method of claim 1, wherein said device lacks a rebreathing chamber.

18. The method of claim 1, wherein the interior volume of said device is approximately 200–500 milliliters.

19. A method for preventing or treating a respiratory condition of a mammal, comprising contacting one nare of said mammal with a drug delivery device for a mammal and delivering an effective dose of a therapeutic composition through said device in a single inhaled breath of said mammal, wherein particles of said therapeutic composition are maintained in a cloud suspension at a size suitable for gaining access to small airways of the lung in said holding chamber prior to inhalation by said mammal, wherein said device comprises a cup-shaped body for enclosing only one external nare, comprises an interfacing lumen the diameter of which does not enclose a second external nare of said mammal; comprises a holding chamber for holding the drug in a cloud suspension, said holding chamber being in communication with said cup-shaped body and comprising a unidirectional inhalation valve located between said holding chamber and said cup-shaped body; does not extend into the nostril or mouth of said mammal; and lacks an exhalation valve.

20. The method of claim 19, wherein said mammal is selected from the group consisting of a horse, a cow, a sheep, and a goat.

21. The method of claim 19, wherein said mammal is a horse.

22. The method of claim 19, wherein said therapeutic composition is administered in the form of a plume of aerosolized particles.

23. The method of claim 22, wherein said particles do no exceed 10 microns in size and wherein said particles are delivered to small airways of the lung.

24. The method of claim 22, wherein said particles are in the size range of 3–5 microns and wherein said particles are delivered to small airways of the lung.

25. The method of claim 19, wherein said therapeutic composition is administered in the form of a dry powder.

26. The method of claim 19, wherein the length of said device is 6–9 inches.

27. The method of claim 19, wherein said device does not enclose the mouth of said mammal.

28. The method of claim 19, wherein said device comprises a patient-actuated inhalation valve.

29. The method of claim 19, wherein said cup–shaped body comprises a flexible interface for contacting the face said mammal.

30. The method of claim 29, wherein said interface is angled.

31. The method of claim 29, wherein said interface is straight.

32. The method of claim 19, wherein said device comprises a spacer holding chamber, said chamber being in communication with said cup–shaped body.

33. The method of claim 32, wherein said chamber comprises a lumen for receiving a therapeutic agent.

34. The method of claim 33, wherein said lumen is adapted to receive an aerosol container.

35. The method of claim 33, wherein said lumen is adapted to receive a metered-dose inhaler (MDI) cannister.

36. The method of claim 19, wherein said device lacks a rebreathing chamber.

37. The method of claim 19, wherein the interior volume of said device is approximately 200–500 milliliters.

38. The method of claim 19, wherein the length of said device is 6–9 inches.

* * * * *